(12) United States Patent
Kis

(10) Patent No.: US 6,291,519 B1
(45) Date of Patent: Sep. 18, 2001

(54) METHOD OF PREVENTING DAMAGE TO EYE TISSUE

(75) Inventor: György Lajos Kis, Triboltingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/415,381

(22) Filed: Oct. 8, 1999

(30) Foreign Application Priority Data

Oct. 14, 1998 (EP) .................................................. 98811021

(51) Int. Cl.⁷ .................................................... A01N 43/16
(52) U.S. Cl. .......................... 514/458; 514/725; 514/912
(58) Field of Search .................................. 514/725, 458, 514/912

(56) References Cited

U.S. PATENT DOCUMENTS

| | | | |
|---|---|---|---|
| 4,999,348 | 3/1991 | Cioca et al. .......................... | 514/171 |
| 5,002,760 | 3/1991 | Katzev ................................... | 424/59 |
| 5,039,513 | 8/1991 | Chatterjee ............................. | 424/47 |
| 5,571,503 | 11/1996 | Mausner ................................. | 424/59 |
| 6,036,946 * | 3/2000 | Greene ................................... | 424/59 |

FOREIGN PATENT DOCUMENTS

| | | |
|---|---|---|
| 0 163 924 A1 | 4/1985 | (EP) . |
| 0 473 159 A1 | 8/1991 | (EP) . |
| 05057754 | 2/1993 | (JP) . |
| WO 97/45105 | 5/1997 | (WO) . |

* cited by examiner

*Primary Examiner*—Zohreh Fay
(74) *Attorney, Agent, or Firm*—David E. Wildman

(57) ABSTRACT

A method for preventing damage to mammalian eye tissues by UV-irradiation and ozone by applying to the eye a pharmaceutically effective amount of vitamin A and vitamin E.

19 Claims, 2 Drawing Sheets

METHOD OF PREVENTING DAMAGE TO EYE TISSUE

The present invention relates to the use of a vitamin cocktail comprising both vitamin A and vitamin E in the preparation of an eye medicament for the protection of the eye against both UV-irradiation and ozone.

Eye medicaments comprising both vitamin A and vitamin E are known in the art. These are for example marketed by CIBA-Vision under the trade name Oculotecto®-Gel. Oculotect is typically prescribed for the treatment of dry eye or keratoconjunctivitis.

It has now surprisingly been found that an ophthalmic composition comprising both vitamin A and vitamin E is highly useful for protecting an eye, in particular the human eye, both against UV-irradiation and ozone exposure, both being typically permanently present as so called environmental toxins.

The ophthalmic compositions useful for the above identified protective treatment of the eye are administered either as a gel, a thermogel, a liquid eye drop or an ointment. Preferred is a gel, thermogel and a liquid composition. More preferred is a gel and a thermogel.

An ophthalmic composition comprises typically the components disclosed infra.

The present invention relates to the use of an ophthalmic composition, which contains mandatorily the two active ingredients vitamin E and vitamin A.

Within the terms of the present invention, vitamin A shall denote a compound such as Vitamin A per se (retinol), esters of retinol such as vitamin A acetate, vitamin A palmitate and the like, retinoic acid and retinoic ester such as retinoic acid methyl ester and the like. Preferred are vitamin A acetate and vitamin A palmitate.

Analogously, vitamin E shall denote within the terms of the present invention vitamin E per se, namely (+)-α-tocopherol, isomers and racemates of α-tocopherol such as racemic DL-α-tocopherol, esters of optically pure and/or racemic α-tocopherol such as DL-α-tocopherol acetate, succinate and/or nicotinate, specific derivatives of α-tocopherol such as D-α-tocopheryl polyethylene glycol 1000 succinate (tocophersolan), tocoretinate (retinoic acid esterified with α-tocopherol, see Merck Index 12th edition, No. 9639) and the like. Preferred are DL-α-tocopherol acetate, tocophersolan and tocoretinate.

Optionally, a vitamin efficacy enhancing agent is present in an above concerned ophthalmic composition, such as aesculin and/or a derivative thereof. Aesculin is a natural product and exhibits an excellent topical tolerability as well.

If present, aesculin is typically present in an amount of 0.001 to approximately 10% by weight, preferably of from 0.05 to 5% by weight and in particular from 0.01–1% by weight.

An ophthalmic composition in accordance to the present invention is advantageously applied topically to the eye, especially in the form of a gel, a thermogel, a solution, a suspension, or an ointment. Such compositions comprise the above vitamins typically in a range of from approximately 0.0005 to approximately 15.0% by weight, preferably from approximately 0.001 to approximately 10.0% by weight, or more preferably in the range of from approximately 0.05 to approximately 7% by weight and most preferably in the range of from 0.01 to 1.1% by weight.

The ratio of a vitamin A to a vitamin E used in an above gel, thermogel or liquid composition is typically from 1:10, more preferably from 1:5 and in particular of from 1:1.

For ointments the ratio of a vitamin A to a vitamin E used is typically from 50:1, more preferably from 35:1 and in particular of from 20:1.

A thermogel denotes a gel which typically exhibits a thermoreversability. A thermogel in accordance to the invention exhibits a viscosity maximum at a temperature in the range of the body temperature and more precisely at a temperature in the range of about 30–60° C. It comprises preferably a polyethylen-polypropylen block copolymer. A representative example of such a block copolymer is Poloxamer 407 (Lutrol® F 127 from BASF, Germany).

Other customary ophthalmically acceptable excipients and additives known to the person skilled in the art may be comprised in an above composition, for example those of the type mentioned below, especially carriers, stabilizers, solubilizers, tonicity enhancing agents, buffer substances, preservatives, thickeners, complexing agents and other excipients. Such compositions are prepared in a manner known per se, for example by mixing the active ingredients with the corresponding excipients and/or additives to form corresponding ophthalmic compositions.

Carriers used in accordance to the present invention are preferably suitable for topical administration, and are for example water, mixtures of water and water-miscible solvents, such as $C_1$- to $C_7$-alkanols, vegetable oils or mineral oils comprising from 0.5 to 5% by weight hydroxyethylcellulose, ethyl oleate, carboxymethylcellulose, polyvinyl-pyrrolidone and other non-toxic water-soluble polymers for ophthalmic uses, such as. for example, cellulose derivatives, such as methylcellulose, alkali metal salts of carboxy-methylcellulose, hydroxymethylcellulose, hydroxyethylcellulose, methylhydroxypropyl-cellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier is, for example, from 1 to 10000 times the concentration of the active ingredient.

Carriers and further ingredients used for ointments are known in the art and are typically those described in example 6 infra.

The solubilizers used for an ophthalmic composition of the present invention are, for example, tyloxapol, fatty acid glycerol polyethylene glycol esters, fatty acid polyethylene glycol esters, polyethylene glycols, glycerol ethers or mixtures of those compounds. A specific example of an especially preferred solubilizer is a reaction product of castor oil and ethylene oxide, for example the commercial products Cremophor EL® or Cremophor RH 40®. Reaction products of castor oil and ethylene oxide have proved to be particularly good solubilizers that are tolerated extremely well by the eye. Another preferred solubilizer is tyloxapol. The concentration used depends especially on the concentration of the active ingredient. The amount added is typically sufficient to solubilize the active ingredient. For example, the concentration of the solubilizer is from 0.1 to 5000 times the concentration of the active ingredient.

Buffers, tonicity enhancing agents and preservatives different from quaternary ammonium salts may be used in an ophthalmic composition of the present invention as well.

Examples of buffer substances are acetate, ascorbate, borate, hydrogen carbonate/carbonate, citrate, gluconate, lactate, phosphate, propionate and TRIS (tromethamine) buffers. Tromethamine and borate buffer are preferred buffers. The amount of buffer substance added is, for example, that necessary to ensure and maintain a physiologically tolerable pH range. The pH range is typically in the range of from 5 to 9, preferably from 5.2 to 8.5 and more preferably from 5.5 to 8.2.

Tonicity enhancing agents are, for example, ionic compounds, such as alkali metal or alkaline earth metal halides, such as, for example, $CaCl_2$, KBr, KCl, LiCl, NaI, NaBr or NaCl, or boric acid. Non-ionic tonicity enhancing agents are, for example, urea, glycerol, sorbitol, mannitol, propylene glycol, or dextrose. For example, sufficient tonicity enhancing agent is added to impart to the ready-for-use ophthalmic composition an osmolality of approximately from 50 to 1000 mOsmol, preferred from 100 to 400 mOsmol, more preferred from 200 to 400 mOsmol and even more preferred from 250 to 350 mOsmol.

Examples of preservatives are quaternary ammonium salts such as benzalkonium chloride, benzoxonium chloride or polyquats (polymeric quaternary ammonium salts, being specifically disclosed in the Canadian Patent No. 1,069,522), alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Preferred preservatives are quaternary ammonium salts, alkyl-mercury salts and parabens. Where appropriate, a sufficient amount of preservative is added to the ophthalmic composition to ensure protection against secondary contaminations during use caused by bacteria and fungi.

The ophthalmic compositions may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. Other excipients that may be used if desired are listed below but they are not intended to limit in any way the scope of the possible excipients. They are especially complexing agents, such as disodium-EDTA or EDTA, antioxidants, such as ascorbic acid, acetylcysteine, cysteine, sodium hydrogen sulfite, butyl-hydroxyanisole, butyl-hydroxytoluene; stabilizers, such thiourea, thiosorbitol, sodium dioctyl sulfosuccinate or monothioglycerol; or other excipients, such as, for example, lauric acid sorbitol ester, triethanol amine oleate or palmitic acid ester. Preferred exipients are complexing agents, such as disodium-EDTA. The amount and type of excipient added is in accordance with the particular requirements and is generally in the range of from approximately 0.0001 to approximately 90% by weight.

The invention also related to method to protect the eye of an individual against UV-irradiation and ozone exposure, which method comprises the regular administration of an ophthalmic composition which comprises both vitamin A and vitamin E to an individual in need therefore.

During summer time, both UV-irradiation and ozone exposure reach a level which may be harmful for the eye. The composition of the present invention is able to filter out the harmful UV-irradiation, in particular UV-A and UV-B irradiation. It has surprisingly been found that the combination of a vitamin A and E exhibit a highly UV-protective effect. In addition to said UV protection, an above composition is simultaneously protecting against ozone. Said ozone is typically deactivated by the antioxidative effect of a vitamin E. In addition to the above protecting effect, the ophthalmic compositions described above are extrmely well tolerated by the eye which allows frequent use.

The invention will be disclosed more particularly in the following, and described by referring to the attached drawing, wherein.

EXAMPLE 1 (gel)

| | |
|---|---|
| 2 g | Collidon 90 F |
| 1 g | $Na_2EDTA$ |
| 15 g | Mowiol (PVA) |
| 0.1 g | benzalkonium chloride (BAK) |
| ad pH 5.7–5.9 | boric acid |
| 10 g | vitamin E, water miscible 0.5 g/g |
| 12 g | vitamin A, water miscible 100'000 IU/g |
| 0.1 g | aesculin |
| ad 1000 ml | water deionized |

EXAMPLE 2 (gel)

| | |
|---|---|
| 0.1 g | benzalkonium chloride (BAK) |
| 1 g | $Na_2EDTA$ |
| 40 g | Mowiol (PVA) |
| ad pH 5.7–5.9 | boric acid |
| 10 g | vitamin E, water miscible 0.5 g/g |
| 12 g | vitamin A, water miscible 100'000 IU/g |
| 0.1 g | aesculin |
| ad 1000 ml | water deionized |

EXAMPlE 3 (thermogel)

| | |
|---|---|
| 0.1 g | benzalkonium chloride (BAK) |
| 1 g | $Na_2EDTA$ |
| 150 g | Lutrol F 127 |
| ad pH 5.7–5.9 | boric acid |
| 10 g | vitamin E, water miscible 0.5 g/g |
| 12 g | vitamin A, water miscible 100'000 IU/g |
| 0.1 g | aesculin |
| ad 1000 ml | water deionized |

EXAMPLE 4 (eye drops)

| | |
|---|---|
| 0.1 g | benzalkonium chloride (BAK) |
| 1 g | $Na_2EDTA$ |
| 40 g | Mowiol (PVA) |
| 1.4 g | borax |
| 16.2 g | boric acid |
| 10 g | α-tocopherol acetate, water miscible 0.5 g/g |
| 10 g | vitamin A palmitate, water miscible 100'000 IU/g |
| 4.0 g | methyl hydroxypropyl cellulose |
| ad 1000 ml | water deionized |

EXAMPLE 5 (gel)

| | |
|---|---|
| 0.1 g | cetrimide |
| 0.5 g | Na₂EDTA |
| 3.5 g | carbomer 980 (carbopol) |
| 5.9 g | tromethamine |
| 16.0 g | glycerol |
| 10 g | α-tocopherol acetate, water miscible 0.5 g/g |
| 10 g | vitamin A palmitate, water miscible 100'000 IU/g |
| ad 1000 ml | water deionized |

EXAMPLE 6 (ointment)

| | |
|---|---|
| 25.7 g | cetyl stearyl alcohol |
| 164.3g | woolfat |
| 252.44 g | liquid paraffin |
| 550.7 g | white petrolatum |
| 0.19 g | α-tocopherol 0.1 mg/g |
| 6.67 g | vitamin A acetate, oily concentrate 1'500'000 IU/g |
| ad 1000 g | ointment |

EXAMPLE 7 (eye drops)

| | |
|---|---|
| 1 g | Na₂EDTA |
| 40 g | Mowiol (PVA) |
| 1.4 g | borax |
| 16.2 g | boric acid |
| 10 g | α-tocopherol acetate, water miscible 0.5 g/g |
| 10 g | vitamin A palmitate, water miscible 100'000 IU/g |
| 4.0 g | methyl hydroxypropyl cellulose |
| ad 1000 ml | water deionized |

EXAMPLE 8 (gel)

| | |
|---|---|
| 0.5 g | Na₂EDTA |
| 3.5 g | carbomer 980 (carbopol) |
| 5.9 g | tromethamine |
| 16.0 g | glycerol |
| 10 g | α-tocopherol acetate, water miscible 0.5 g/g |
| 10 g | vitamin A palmitate, water miscible 100'000 IU/g |
| ad 1000 ml | water deionized |

EXAMPLE 9

1.25 g gel of example 5 is diluted in 100 ml of deionized water. This highly diluted solution is investigated by UV-spectroscopy (see FIG. 1), which demonstrates that the addressed ophthalmic gel exhibits a significant UV-absorption even at low concentration (simulation of the tear dilution effect when administering the gel to the eye).

Figure 1:
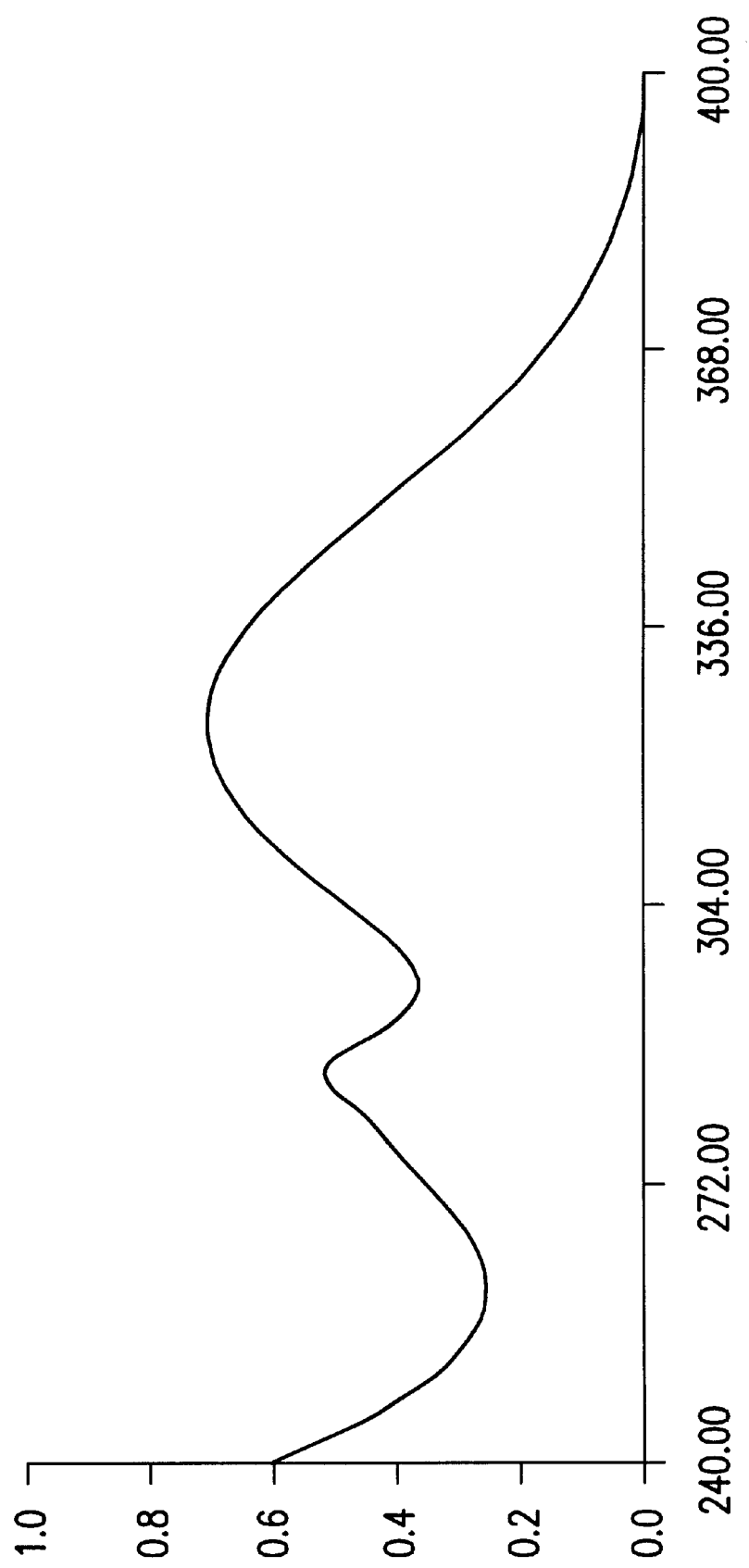
FIG. 1 shows a UV-spectrum of a gel in accordance to example 5, which has been diluted in water (1.25 g gel in 100 ml water).

The UV spectrum of FIG. 1 is recorded with a Perkin Elmer, Lambda 15 UV/VIS spectrophotometer. Two maxima are recorded, namely at 329.2 nm (0.705 relative absorption) and at 286.4 nm (0.539 relative absorption).

EXAMPLE 10

Figure 2:
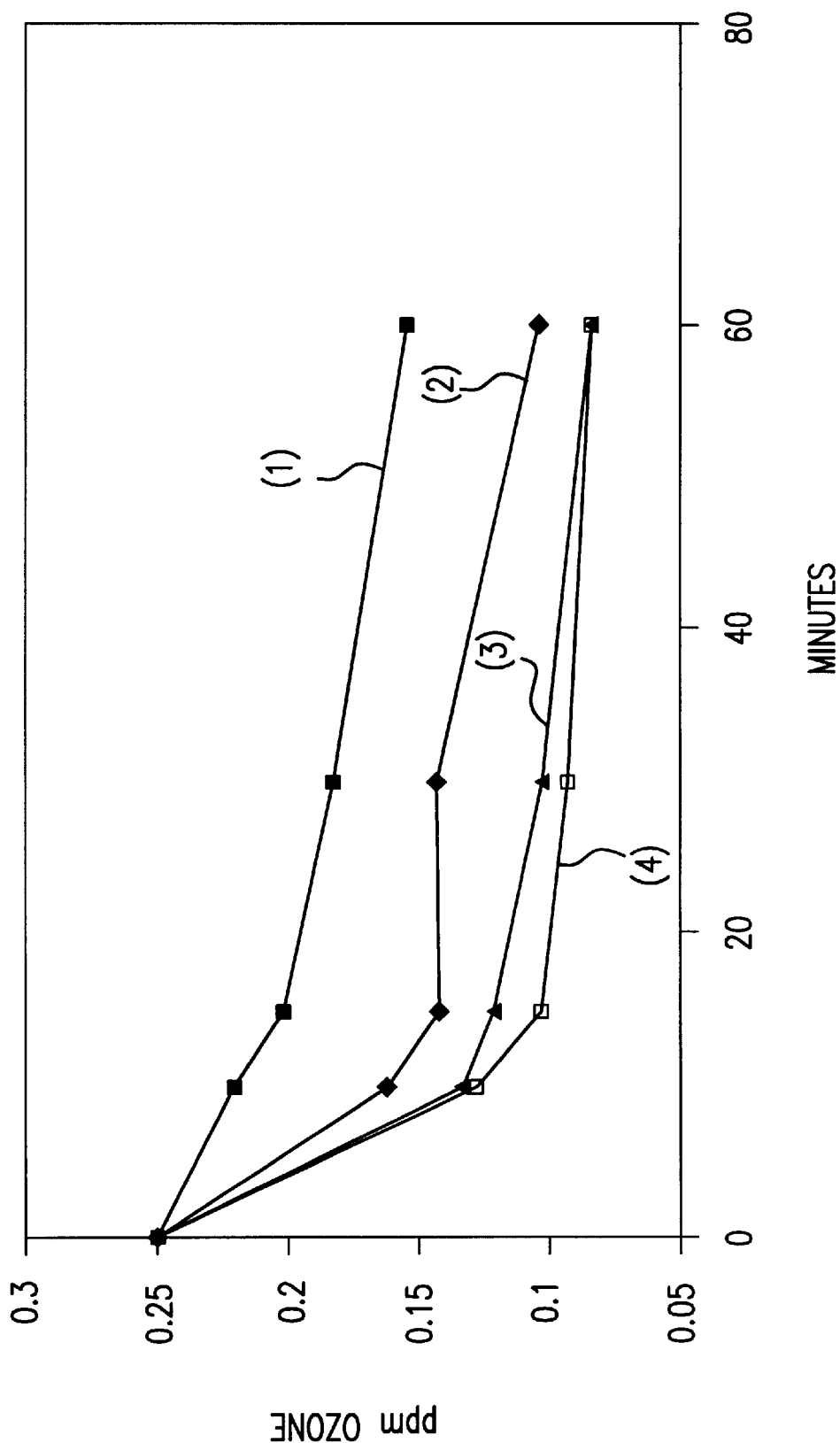
FIG. 2 shows graphially the ozone degrading efficacy of a composition comprising both vitamin A and E in water. The top curve shows the ozone degradation in water per se.

The ozone protective effect is investigated by the determination of the ozone degradation in water (see FIG. 2). The ozone concentration in ppm (parts per million) is shown on the Y-axis (ordinate) of the diagramm. The time in minutes (abscissa) is disclosed on the X-axis.

Curve (1) shows the ozone degradation by time of 0.25 ppm ozone in pure deionized water (untreated water).

Curves (2), (3) and (4) show the ozone degradation by time of 0.25 ppm ozone in water, with the proviso that:

1 g gel (example 5) per 100 ml water is present, curve (2);
2 g gel (example 5) per 100 ml water is present, curve (3);
4 g gel (example 5) per 100 ml water is present, curve (4).
(Water saturated with ozone contains 0.25 ppm ozone)

What is claimed is:

1. A method for preventing damage to mammalian eye tissues by UV-irradiation, ozone, or both comprising administering to the eye of a subject, wherein the eye is exposed to UV-irradiation, ozone, or both at a level that is harmful to the eye, an amount of an eye medicament comprising an amount of vitamin A and an amount of vitamin E effective to absorb UV-irradiation, destroy ozone, or both absorb UV-irradiation and destroy ozone.

2. A method as claimed in claim 1, wherein the eye medicament is a gel, thermogel, eye drop or ointment.

3. A method as claimed in claim 1, wherein the eye medicament is a gel or thermogel.

4. A method as claimed in claim 1, wherein the eye medicament further comprises aesculin.

5. A method as claimed in claim 1, wherein the eye medicament further comprises a preservative.

6. A method as claimed in claim 1, wherein the eye medicament further comprises a buffer.

7. A method as claimed in claim 6, wherein the pH of the medicament is in the range of 5.5–8.2.

8. A method as claimed in claim 1, wherein the vitamin A is selected from the group consisting of vitamin A per se (retinol), esters of retinol, retinoic acid and retinoic ester.

9. A method as claimed in claim 1, wherein the vitamin E is selected from the group consisting of vitamin E per se, isomers and racemates of α-tocopherol, esters of optically pure and/or racemic α-tocopherol specific derivatives of α-tocopherol and tocoretinate (retinoic acid esterified with α-tocopherol).

10. A method as claimed in claim 1, wherein UV-irradiation denotes the wavelength spectrum of UV-A and UV-B (280–400 nm).

11. A method as claimed in claim 8, wherein the vitamin A is selected from the group consisting of retinol, vitamin A acetate, vitamin A palmitate, retinoic acid, and retinoic acid methyl ester.

12. A method as claimed in claim 11, wherein the vitamin A is selected from the group consisting of vitamin A acetate and vitamin A palmitate.

13. A method as claimed in claim 9, wherein the vitamin E is selected from the group consisting of (+)-α-tocopherol, racemic DL-α-tocopherol, DL-α-tocopherol acetate, DL-α-tocopherol succinate, DL-α-tocopherol nicotinate, D-α-tocopheryl polyethylene glycol 1000 succinate (tocophersolan), and tocoretinate.

14. A method as claimed in claim 13, wherein the vitamin E is selected from the group consisting of DL-α-tocopherol acetate, tocophersolan, and tocoretinate.

15. A method as claimed in claim 2, wherein the ratio of vitamin A to vitamin E is 20:1.

16. A method as claimed in claim 3, wherein the ratio of vitamin A to vitamin E is 1:1.

17. A method as claimed in claim 2, wherein the combination of vitamin A and vitamin E is from 0.01% to 1.1%, by weight, of the eye medicament.

18. A method as claimed in claim 2, wherein the medicament is administered topically in the form of eye drops.

19. A method as claimed in claim 18, wherein the eye drops are applied at the rate of one drop; one to three times a day.

* * * * *